United States Patent [19]

Howe et al.

[11] Patent Number: 4,461,642

[45] Date of Patent: Jul. 24, 1984

[54] HERBICIDAL COMPOSITIONS AND METHOD

[75] Inventors: Robert K. Howe, Bridgeton; Len F. Lee, St. Charles, both of Mo.

[73] Assignee: Monsanto Company, St. Louis, Mo.

[21] Appl. No.: 356,012

[22] Filed: Mar. 8, 1982

[51] Int. Cl.$^3$ ............... A01N 43/36; C07D 207/333
[52] U.S. Cl. ........................................ 71/95; 71/88; 71/90; 71/91; 71/92; 71/13; 71/94; 548/536
[58] Field of Search ............................ 548/536; 71/95

[56] References Cited

U.S. PATENT DOCUMENTS

| | | | |
|---|---|---|---|
| 2,744,915 | 5/1956 | Jones et al. | 548/536 |
| 3,197,480 | 7/1965 | England | 548/560 |
| 3,285,931 | 11/1966 | Huisgen | 548/560 X |
| 3,442,913 | 5/1969 | Wyckoff et al. | 549/504 X |
| 3,999,975 | 12/1976 | Steinhards | 71/95 |
| 4,194,003 | 3/1980 | Laforest et al. | 548/531 X |
| 4,290,940 | 9/1981 | Wirth et al. | 548/560 X |

OTHER PUBLICATIONS

C.A., 33, 2900$^9$, Fischer et al., (1939).
Noller, "The Chemistry of Organic Compounds", 1965, 3rd Ed., p. 803, W. B. Saunders Co., Philadelphia, Penna., U.S.A.

*Primary Examiner*—Joseph Paul Brust
*Attorney, Agent, or Firm*—J. Timothy Keane; Raymond C. Loyer; Richard H. Shear

[57] ABSTRACT

The invention herein pertains to novel 2,5-bis-(perfluoroalkyl)-3,4-pyrroledicarboxylates and a method for their preparation. The novel pyrroles have been found to have utility as pre- and postemergent herbicides.

13 Claims, No Drawings

HERBICIDAL COMPOSITIONS AND METHOD

This invention relates to compounds useful as herbicides. The compounds may be represented by the structural formula

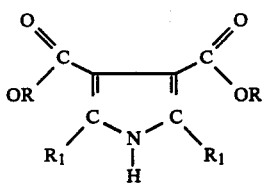

wherein R represents a lower alkyl radical and $R_1$ represents a perfluoroalkyl radical.

The term "lower alkyl" as employed herein is intended to mean alkyl radicals having from 1 to 4 carbon atoms, inclusively.

The term "perfluoroalkyl" as employed herein is intended to mean alkyl radicals having from 1 to 3 carbon atoms, inclusively, wherein all of the hydrogen atoms have been replaced with fluorine atoms.

In accordance with one of the novel aspects of this invention, the above-described pyrroles can be prepared by the reaction of an appropriate β-aminoacrylate and either sulfur mono- or dichloride. Said reaction produces a mixture of the above pyrrole and 3,5-bis-perfluoroalkyl 2H-1,4-thiazine-2,6-dicarboxylates.

While the pyrrole compounds can be easily separated from the reaction mixture such as by chromatography it has been discovered that the above-mentioned thiazine can be easily converted, in high yield, to the corresponding pyrrole by treatment with an amine base.

The preparation of the pyrroles of this invention by the reaction of a sulfur chloride with β-aminoacrylate may be described as follows:

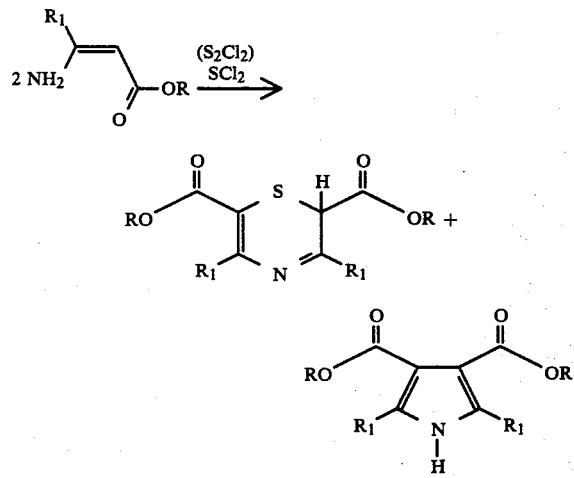

The product of the above reaction can be readily separated by HPLC on silica gel using ethyl acetate-petroleum ether as eluant. The above reaction is typically initiated at relatively low temperatures such as −5° C. to +5° C. The reaction mixture is allowed to warm as the reaction proceeds and addition of heat is applied as the temperature reaches ambient condition. Generally, the reaction is completed at a temperature in the range of from 40° C. to 60° C. Although not critical, the reaction time extends for a period of about 3 hours at the elevated temperature. However, individual reactants have varying reaction rates and, of course, temperature level also affects the reaction rate.

As mentioned above, either sulfur monochloride or sulfur dichloride may be employed. However, experience indicates that higher yields of the desired pyrroledicarboxylate is obtained utilizing sulfur dichloride. More importantly, the order of addition of the reactants influence the product mixture. A nearly equal amount of the desired pyrroledicarboxylate and thiazinedicarboxylate are produced when the sulfur chloride is added to the β-aminoacrylate. However, should the order of addition be reversed, the thiazinedicarboxylate will constitute the major amount of the reaction product.

Any suitable reaction medium may be employed and typically they are selected from the common organic hydrocarbons and halogenated hydrocarbons. Typical reaction media ae chlorobenzene, $C_{6-10}$ hydrocarbons such as hexane and commercially available mixed hydrocarbons.

The thiazinedicarboxylate provided by the above reaction I can be utilized to provide the pyrroledicarboxylates of this invention in accordance with the following reaction:

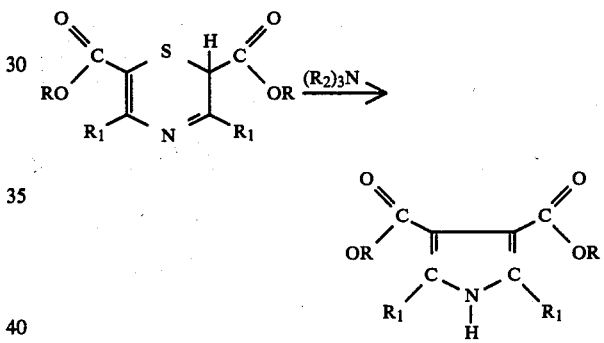

wherein R and $R_1$ are as defined above, $R_2$ is selected from lower alkyl and hydrogen. The reaction proceeds at room temperature for a period of from about 1 to about 4 hours. Typically a suitable solvent is employed such as the ethers, for example ethyl ether.

Accordingly, one may provide the pyrroledicarboxylates of this invention in high yield by recovering the pyrroledicarboxylates produced by the reaction of sulfur chloride and β-aminoacrylate and then reacting the thiazine also produced by treatment with an amine base.

The β-aminoacrylates utilized in the above-described reaction may be prepared according to known procedures such as that specified by Lutz et al, JOURNAL OF HETEROCYCLIC CHEMISTRY, Volume 9, Page 513 (1972) or they may be prepared by mixing 0.5 moles of ethyl acetoacetate or methyl acetoacetate in 200 ml. of methanol and 100 ml. of saturated sodium acetate and passing through the appropriate nitrile (perfluorinated if R is to be perfluorinated) for several hours. The reaction mixture is poured into ice water and the organic layer extracted with ether. The ether solution is dried and concentrated and the residue is distilled. A mixture of about 0.1 mole of said distillate and 50 ml. of 30% ammonium hydroxide or sodium hydroxide is stirred from 1 to 2 hours. The reaction mixture is extracted with methylene chloride and the methylene chloride extracts dried and concentrated. Fractional distillation of the residue results in the β-aminoacrylate.

In order to more fully describe the manner in which the pyrroledicarboxylates of this invention are prepared, the following non-limiting examples are presented.

EXAMPLE 1

Preparation of Thiazinedicarboxylate

There is described below the preparation of various thiazines which are utilized in the following examples to provide the pyrroledicarboxylate of this invention.

1a

To a well stirred cold ($-3°$ C.) solution of 2.1 g (0.02 mol) of $SCl_2$ in 100 ml. of chlorobenzene is added dropwise a solution of 9.32 g (0.04 mol) of ethyl 3-amino-4,4,5,5,5-pentafluoro-2-pentenoate in 10 ml. of chlorobenzene in 10 minutes. The reaction mixture is heated to 50° C. in 55 minutes and maintained at 50° C. for 3 hours. The reaction mixture is filtered and washed with hexane. The combined filtrate is concentrated under reduced pressure and the residual oil (10.4 g) is kugelrohr distilled at 1 mm (pot temperature 110° C.) to give 7.96 g (83%) of the desired product $n_D^{25}$ 1.4140.

Anal. Calc'd for $C_{14}H_{11}F_{10}NO_4S$: C, 35.08; H, 2.31; N, 2.92. Found: C, 35.39; H, 2.15; N, 2.96.

In a manner similar to Example 1a, other thiazines are prepared by the reaction of the appropriate β-aminoacrylate and sulfur chloride as indicated below in Table I.

TABLE I

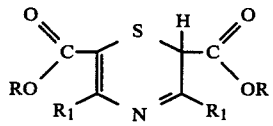

| Ex. No. | R | $R_1$ | Chloride | M.P. °C. | $N_D^{25}$ | Empirical Formula | Analysis Calc'd | | | Found | | |
|---|---|---|---|---|---|---|---|---|---|---|---|---|
| | | | | | | | C | H | N | C | H | N |
| 1b | $C_2H_5$ | $CF_3$ | $S_2Cl_2$ | | 1.4395 | $C_{12}H_{11}F_6NO_4S$ | 38.00 | 2.92 | 3.69 | 38.15 | 2.98 | 3.69 |
| 1c | $CH_3$ | $C_2F_5$ | $SCl_2$ | 33.5-36 | | $C_{12}H_7F_{10}NO_4S$ | 31.94 | 1.56 | 3.10 | 31.91 | 1.58 | 3.10 |

EXAMPLE 2

Preparation of Diethyl 2,5-bis(pentafluoroethyl)-3,4-pyrroledicarboxylate

To a solution of 4.36 g (0.00909 mol) of the compound of Example 1a in 20 ml. of ether is added 0.92 g (0.00909 mol) of triethylamine. The reaction mixture is stirred for 10 minutes and concentrated under reduced pressure. NMR analysis of the residue indicates that the reaction is not complete and there is added to the residue 0.5 g of triethylamine and 20 ml. of ether. The mixture is held at reflux for 1 hour, cooled and filtered. The ether filtrate is washed with diluted HCl, dried (MgSO4) and concentrated under reduced pressure to give 4.6 g of oil which is chromatographed on silica gel, using methylenedichloride as eluant. The desired product (Rf=0.27) is obtained as an oil (3.5 g) which when crystallized from petroleum ether yields 2.54 g (62.5%) of the desired product, mp 64.5°-65.5° C.

Anal. Calc'd for $C_{14}H_{11}F_{10}NO_4$: C, 37.70; H, 2.48; N, 3.13 Found: C, 37.93; H, 2.28 N, 3.15

EXAMPLE 3

Preparation of Diethyl 2,5-bis(perfluoropropyl)-3,4-pyrroledicarboxylate

In a manner similar to Example 1, diethyl 2,5-bis(perfluoropropyl)-3,4-pyrroledicarboxylate is prepared by the reaction of 3-perfluoropropyl-3-aminoacrylate and sulfur monochloride. The reaction mixture is triturated with 200 ml. of hexane and cooled with a dry ice bath. The insoluble material is filtered to provide 8.2 g. of solid which is a hydrochloride salt mixture of thiazine and pyrroledicarboxylates. The solid is dissolved in ether, washed with water, dried (Mg SO4) and concentrated to give 7 g. of an oil which, upon analysis, is found to contain 47% of the desired product and 53% of diethyl 3,5-(perfluoropropyl)-2H-1,4-thiazine-2,6-dicarboxylate. The oil is purified by HPLC on silica gel using ethylacetate-petroleum ether (8:92, v/v) as eluant. The first fraction is the desired product mp 70.5°-73.5° C.

Anal. Calc'd for $C_{16}H_{13}F_{14}$: C, 35.11; H, 2.03; N, 2.56. Found: C, 35.41; H, 2.07; N, 2.58.

EXAMPLE 4

Diethyl 2,5-bis-(trifluoromethyl)-3,4-pyrrole-dicarboxylate

To 3.8 g (0.01 mol) of the compound of Example 1b is added 1.0 g (0.01 mol) of triethylamine. An exothermic reaction occurs immediately. To the reaction mixture is added toluene and the reaction mixture is stirred for 30 minutes and filtered to give 0.13 g of sulfur, mp 118°-120° C. soften. The toluene filtrate is concentrated under reduced pressure to give 3.8 g of oil which Kugelrohr distilled at 1 mm (pot temperature 130° C.) to give 3.1 g of oil which is chromatographed on silica gel. The first fraction (from 0.5 of 5% ethyl acetate petroleum ether) is 0.1 g of sulfur. The second fraction (from 1.2 of 10% ethyl acetate) is 2.3 g of oil which is crystallized at low temperature from petroleum ether to give 2.0 g (57%) of the desired product, mp 55°-57° C.

Anal. Calc'd for $C_{12}H_{11}F_4NO$: C, 41.51; H, 3.19; N, 4.03. Found: C, 41.51; H, 3.19; N, 4.01.

EXAMPLE 5

Preparation of Dimethyl 2,5-bis(pentafluoroethyl)-3,4-pyrroledicarboxylate

To a solution of 7.00 g (0.0155 mole) of the compound of Example 1c in 20 ml. of ether is added 1.57 g (0.0155 mole) of triethylamine. The reaction mixture is stirred for 1 hour and filtered. The filtrate is washed with diluted hydrochloric acid, dried (MgSO4) and concentrated. The residue is kugelrohr distilled at 1.5 mm (pot temperature 120° C.) to give 6.25 g of an oil which is chromatographed on silica gel using ether-petroleum ether (2:3) as eluant to give 5.96 g (92%) of desired product, mp 68°–71° C.

Anal. Calc'd for $C_{12}H_7F_{10}N_1O_4$: C, 34.46; H, 1.69; N, 3.35; Found: C, 34.36; H, 1.71; N, 3.34.

As noted above, the compounds of this invention have been found to be effective as herbicides, in some instances both pre-emergent as well as post-emergent. Tables II and III summarize results of tests conducted to determine the pre-emergent herbicidal activity of the compounds of this invention. Table IV and V summarize results of tests conducted to determine the post-emergent herbicidal activity of the compounds of this invention.

The pre-emergent tests are conducted as follows:

A good grade of top soil is placed in aluminum pans and compacted to a depth of three-eighths to one-half inch from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable powder suspension and the soil are thoroughly mixed, and used as a cover layer for prepared pans. After treatment, the pans are moved into a greenhouse bench where they are watered from below as needed to give adequate moisture for germination and growth.

Approximately 2–3 weeks after seeding and treating, the plants are observed and the results recorded. Table II below summarizes such results. The herbicidal rating is obtained by means of a fixed scale based on the percent injury of each plant species. The ratings are defined as follows:

| % Control | Rating |
|---|---|
| 0–24 | 0 |
| 25–49 | 1 |
| 50–74 | 2 |
| 75–100 | 3 |

The plant species utilized in one set of tests, the data for which are shown in Table II, are identified by letter in accordance with the following legend:

| | | |
|---|---|---|
| A Canada Thistle* | E Lambsquarters | I Johnsongrass* |
| B Cocklebur | F Smartweed | J Downy Brome |
| C Velvetleaf | G Yellow Nutsedge* | K Barnyardgrass |
| D Morningglory | H Quackgrass* | |

*Grown from vegetative propagules

TABLE II

Pre-Emergent

| Compound of Example No. | WAT | kg/h | A | B | C | D | E | F | G | H | I | J | K |
|---|---|---|---|---|---|---|---|---|---|---|---|---|---|
| 4 | 2 | 11.2 | 1 | 0 | 3 | — | 3 | 0 | 0 | 0 | 0 | 0 | 0 |
| 3 | 2 | 11.2 | 0 | 0 | 0 | 1 | 3 | 3 | 0 | 0 | 0 | 1 | 2 |
| 2 | 2 | 11.2 | 0 | 1 | 3 | 3 | 3 | 3 | 0 | 1 | 0 | 0 | 0 |
| 5 | 2 | 11.2 | 2 | 0 | 1 | 3 | 2 | 0 | 0 | 0 | 0 | 0 | 3 |
| | 4 | 11.2 | 1 | 0 | 1 | 2 | 3 | 0 | 0 | 0 | 0 | 0 | 3 |

The compounds were further tested by utilizing the above procedure on the following plant species:

| | | | | |
|---|---|---|---|---|
| L | Soybean | R | Hemp Sesbania |
| M | Sugarbeet | E | Lambsquarters |
| N | Wheat | F | Smartweed |
| O | Rice | C | Velvetleaf |
| P | Sorghum | J | Downy Brome |
| B | Cocklebur | S | Panicum |
| Q | Wild Buckwheat | K | Barnyardgrass |
| D | Morningglory | T | Crabgrass |

The results are summarized in Table III.

TABLE III

Pre-Emergent

| Compound of Example No. | kg/ha | L | M | N | O | P | B | Q | D | R | E | F | C | J | S | K | T |
|---|---|---|---|---|---|---|---|---|---|---|---|---|---|---|---|---|---|
| 4 | 5.6 | 0 | 3 | 0 | 0 | 0 | 0 | 0 | 3 | 2 | 3 | 0 | 3 | 0 | 0 | 0 | 0 |
| | 1.12 | 0 | 1 | 0 | 0 | 0 | 0 | 0 | 0 | 0 | 1 | 0 | 1 | 0 | 0 | 1 | 0 |
| 3 | 5.6 | 0 | 2 | 0 | 0 | 0 | 0 | 1 | 0 | 0 | 3 | 2 | 0 | 1 | 0 | 0 | 1 |
| | 1.12 | 0 | 3 | 0 | 0 | 0 | 0 | 0 | 1 | 2 | 0 | 0 | 0 | 0 | 0 | 0 | 0 |
| 2 | 5.6 | 0 | 3 | 1 | 0 | 0 | 0 | 1 | 2 | 3 | 3 | 3 | 3 | 0 | 0 | 0 | 2 |
| | 1.12 | 0 | 3 | 0 | 0 | 0 | — | 1 | 1 | 2 | 3 | 2 | 1 | 0 | 0 | 0 | 2 |
| | .28 | 0 | 3 | 0 | 0 | 0 | 0 | 0 | 0 | 3 | 0 | 0 | 0 | 0 | 0 | 0 | 2 |
| 5 | 5.6 | 0 | 3 | 0 | 0 | 0 | 0 | 1 | 2 | 2 | 3 | 1 | 0 | 3 | 1 | 2 | — |
| | 1.12 | 0 | 0 | 0 | 0 | 0 | 0 | 0 | 1 | 1 | 1 | 0 | 0 | 0 | 0 | 1 | — |

The post-emergent tests were conducted as follows. The herbicidal active ingredients were applied in spray form to two or three-week old specimens of various plant species. The spray, a solution or wettable powder suspension containing the appropriate rate of herbicidal active ingredient to give the desired test rate and a surfactant, was applied to the plants at a pressure of 3.62 g/mm². The surfactant is an amine salt of an alkylbenzenesulfonic acid blended with an ethoxylated tall oil. The spray volume is regulated to apply at a rate of about 850 L/ha. The treated plants were placed in a greenhouse and approximately two or four weeks later the effects were observed and recorded. The results are shown in Tables IV and V in which the post-emergent herbicidal rating code is as follows:

| % Control | Rating |
|---|---|
| 0–24 | 0 |
| 25–49 | 1 |
| 50–74 | 2 |
| 75–99 | 3 |

-continued

| % Control | Rating |
|---|---|
| 100 | 4 |

The plant species utilized in these tests are identified by letter in accordance with the previous legend.

TABLE IV

| Compound of Example No. | WAT | kg/h | Post-Emergent Plant Species | | | | | | | | | | |
|---|---|---|---|---|---|---|---|---|---|---|---|---|---|
| | | | A | B | C | D | E | F | G | H | I | J | K |
| 4 | 2 | 11.2 | 2 | 3 | 2 | 4 | 3 | 3 | 0 | 0 | 1 | 1 | 3 |
| 3 | 2 | 11.2 | — | 1 | 0 | 1 | 1 | 0 | 0 | 0 | 0 | 0 | 1 |
| 2 | 2 | 11.2 | 1 | 3 | 4 | 2 | 4 | 4 | 0 | 0 | 0 | 1 | 0 |
| 5 | 2 | 11.2 | 0 | 0 | 0 | 0 | 1 | 0 | — | 0 | 0 | 0 | 0 |

TABLE V

| Compound of Example No. | kg/ha | Post-Emergent Plant Species | | | | | | | | | | | | | |
|---|---|---|---|---|---|---|---|---|---|---|---|---|---|---|---|
| | | L | M | N | O | P | B | Q | D | R | E | F | C | J | S | K | T |
| 4 | 5.6 | 2 | 4 | 0 | 0 | 1 | 3 | 1 | 3 | 4 | 3 | 4 | 2 | 0 | 3 | 3 | 1 |
| | 1.12 | 1 | 0 | 0 | 0 | 0 | 0 | 0 | 1 | 3 | 1 | 0 | 0 | 0 | 0 | 0 | 1 |
| | .28 | 1 | 0 | 0 | 0 | 0 | 0 | 0 | 1 | 0 | 0 | 0 | 0 | 0 | 0 | 0 | 0 |
| 2 | 5.6 | 4 | 4 | 3 | 2 | 3 | 4 | 4 | 4 | 4 | 4 | 4 | 3 | 2 | 1 | 3 | 3 |
| | 1.12 | 1 | 4 | 1 | 0 | 1 | 3 | 1 | 2 | 4 | 4 | 1 | 0 | 0 | 2 | 2 |
| | .28 | 1 | 4 | 0 | 0 | 0 | 1 | 2 | 0 | 4 | — | 1 | 0 | 0 | 0 | 1 | 1 |

The above tables illustrate one aspect of the present invention, that is, the use of the compounds of the invention to kill or injure undesirable plants, e.g., weeds.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total suspension, preferably 480 to 600 g/l.

Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium

Ureas

N'-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
Ethyl N,N-dipropylthiolcarbamate
S-propyl dipropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[(trifluoromethyl)sulfonyl amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl) glycine and its $C_{1-6}$ monoalkyl amine and alkaline metal salts and combinations thereof

Ethers 2,4-Dichlorophenyl-4-nitrophenyl ether
2-Chloro-α,α,α-trifluoro-p-tolyl-3-ethoxy-4-nitrodiphenyl ether

Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 2 | 1.0 |
| | Free acid of complex organic phosphate of aromatic or aliphatic hydrophobe base (e.g., GAFAC RE-610, registered trademark of GAF Corp) | 5.59 |

-continued

|   |   | Weight Percent |
|---|---|---|
|   | Polyoxyethylene/polyoxypropylene block copolymer with butanol (e.g., Tergitol XH, registered trademark of Union Corp.) | 1.11 |
|   | Phenol | 5.34 |
|   | Monochlorobenzene | 77.16 |
|   |   | 100.00 |
| B. | Compound of Example No. 3 | 25.00 |
|   | Free acid of complex organic phosphate of aromatic or aliphatic hydrophobe base (e.g., GAFAC RE-610) | 5.00 |
|   | Polyoxyethylene/polyoxypropylene block copolymer with butanol (e.g., Tergitol XH) | 1.60 |
|   | Phenol | 4.75 |
|   | Monochlorobenzene | 63.65 |
|   |   | 100.00 |
| II. Flowables | | |
| A. | Compound of Example No. 2 | 25.00 |
|   | Methyl cellulose | 0.3 |
|   | Silica aerogel | 1.5 |
|   | Sodium lignosulfonate | 3.5 |
|   | Sodium N—methyl-N—oleyl taurate | 2.0 |
|   | Water | 66.7 |
|   |   | 100.00 |
| B. | Compound of Example No. 4 | 45.0 |
|   | Methyl cellulose | .3 |
|   | Silica aerogel | 1.5 |
|   | Sodium lignosulfonate | 3.5 |
|   | Sodium N—methyl-N—oleyl taurate | 2.0 |
|   | Water | 47.3 |
|   |   | 100.00 |
| III Wettable Powders | | |
| A. | Compound of Example No. 4 | 25.0 |
|   | Sodium lignosulfonate | 3.0 |
|   | Sodium N—methyl-N—oleyl-taurate | 1.0 |
|   | Amorphous silica (synthetic) | 71.0 |
|   |   | 100.00 |
| B. | Compound of Example No. 2 | 80.0 |
|   | Sodium dioctyl sulfosuccinate | 1.25 |
|   | Calcium lignosulfonate | 2.75 |
|   | Amorphous silica (synthetic) | 16.00 |
|   |   | 100.00 |
| C. | Compound of Example No. 3 | 10.00 |
|   | Sodium lignosulfonate | 3.0 |
|   | Sodium N—methyl-N—oleyl-taurate | 1.0 |
|   | Kaolinite clay | 86.0 |
|   |   | 100.00 |
| IV. Water-Soluble Powders | | |
| A. | Compound of Example 5 | 10.0 |
|   | Sodium dioctyl sulfosuccinate | 2.0 |
|   | Silica aerogel | 5.0 |
|   | Methyl violet | 0.1 |
|   | Sodium bicarbonate | 82.9 |
|   |   | 100.00 |
| B. | Compound of Example No. 2 | 90.0 |
|   | Ammonium phosphate | 10.0 |
|   |   | 100.00 |
| V. Dusts | | |
| A. | Compound of Example No. 4 | 2.0 |
|   | Attapulgite | 98.0 |
|   |   | 100.00 |
| B. | Compound of Example No. 2 | 60.0 |
|   | Montmorillonite | 40.0 |
|   |   | 100.00 |
| C. | Compound of Example No. 2 (cis) | 30.0 |
|   | Ethylene glycol | 1.0 |
|   | Bentonite | 69.0 |
|   |   | 100.00 |
| D. | Compound of Example No. 4 | 1.0 |
|   | Diatomaceous earth | 99.0 |
|   |   | 100.00. |
| VI. Granules | | |

-continued

|   |   | Weight Percent |
|---|---|---|
| A. | Compound of Example No. 3 | 15.0 |
|   | Granular attapulgite (20/40 mesh) | 85.0 |
|   |   | 100.00 |
| B. | Compound of Example No. 5 | 30.0 |
|   | Diatomaceous earth (20/40) | 70.0 |
|   |   | 100.00 |
| C. | Compound of Example No. 5 | 1.0 |
|   | Ethylene glycol | 5.0 |
|   | Methylene blue | 0.1 |
|   | Pyrophyllite | 93.9 |
|   |   | 100.00 |
| D. | Compound of Example No. 2 | 5.0 |
|   | Pyrophyllite (20/40) | 95.0 |
|   |   | 100.00 |

When operating in accordance with the present invention, effective amounts of the compounds of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific compounds employed. In selective preemergence application to the plants or to the soil a dosage of from 0.02 to about 11.2 kg/ha, preferably from about 0.04 to about 5.60 kg/ha, or suitably from 1.2 to 5.6 kg/ha of herbicide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

We claim:

1. A method for controlling the growth of undesirable plants which comprises applying to the locus of the seed a herbicidal amount of a compound represented by the formula

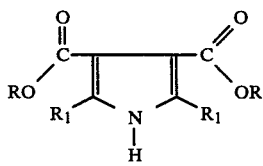

wherein R represents a lower alkyl radical having 1 to 4 carbon atoms and $R_1$ represents a perfluoroalkyl radical having from 1 to 3 carbon atoms.

2. A method of claim 1 wherein R is ethyl and $R_1$ is perfluoroalkyl.

3. A method of claim 1 wherein R is ethyl and $R_1$ is trifluoromethyl.

4. A method of claim 1 wherein R is ethyl and $R_1$ is perfluoropropyl.

5. A method of claim 1 wherein R is methyl and $R_1$ is perfluoromethyl.

6. A method for controlling the growth of undesirable plants which comprises applying to the plant a herbicidally effective amount of a compound represented by the formula

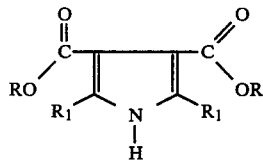

wherein R represents lower alkyl radical having 1 to 4 carbon atoms and $R_1$ represents a perfluoroalkyl radical having from 1 to 3 carbon atoms.

7. A method of claim 6 wherein R is ethyl and $R_1$ is perfluoroethyl.

8. A method of claim 6 wherein R is ethyl and $R_1$ is trifluoromethyl.

9. A method of claim 6 wherein R is ethyl and $R_1$ is perfluoropropyl.

10. A process for preparing a compound of the formula

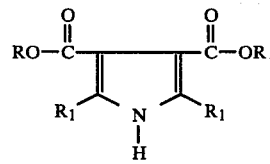

wherein R and $R_1$ are as defined hereinbelow, which comprises reacting a compound represented by the formula:

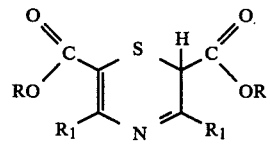

wherein R represents a lower alkyl radical having 1 to 4 carbon atoms and $R_1$ represents a perfluoroalkyl radical having 1 to 3 carbon atoms, with an alkyl amine represented by the formula:

$(R_2)_3N$ wherein $R_2$ is selected from lower alkyl of 1 to 4 carbon atoms and hydrogen.

11. The process of claim 10 wherein the alkyl amine is triethylamine.

12. The process of claim 10 wherein R is ethyl and $R_1$ is trifluoromethyl.

13. The process of claim 10 wherein R ethyl and $R_1$ is perfluoroethyl.

* * * * *

UNITED STATES PATENT AND TRADEMARK OFFICE
CERTIFICATE OF CORRECTION

PATENT NO. : 4,461,642

DATED : July 24, 1984

INVENTOR(S) : Robert K. Howe and Len F. Lee

It is certified that error appears in the above-identified patent and that said Letters Patent is hereby corrected as shown below:

Column 13, Claim 5, line 19: "perfluoromethyl" should be --perfluoroethyl--

Signed and Sealed this

Eighteenth Day of December 1984

[SEAL]

Attest:

Attesting Officer

GERALD J. MOSSINGHOFF

Commissioner of Patents and Trademarks